United States Patent [19]
Hajimichael et al.

[11] Patent Number: 5,455,237
[45] Date of Patent: Oct. 3, 1995

[54] ACARICAIDALLY ACTIVE TETRAZINE DERIVATIVES

[75] Inventors: Janis Hajimichael; Sándor Botár; Edit Bleicher; László Pap, all of Budapest; István Székely, Dunakeszi; Katalin Mármarosi, Biatorbágy; János Öri, Budapest, all of Hungary

[73] Assignee: Chinoin Gyogyszer Es Vegyeszeti Termekek Gyara RT., Budapest, Hungary

[21] Appl. No.: 277,800

[22] Filed: Jul. 20, 1994

[30] Foreign Application Priority Data

Jul. 21, 1993 [HU] Hungary ................................. 2098/93

[51] Int. Cl.$^6$ ...................... C07D 257/08; A01N 43/713
[52] U.S. Cl. ............................................. 514/183; 544/179
[58] Field of Search ............................. 544/179; 514/183

[56] References Cited

U.S. PATENT DOCUMENTS 4,237,127 12/1980 Parsons ................................... 544/179

FOREIGN PATENT DOCUMENTS 005912 12/1979 European Pat. Off. .

OTHER PUBLICATIONS

Chem. Abstracts 60:13370d (1964).
Chem. Abstracts 98 24446z (1983).
Brooker et al, Pestic. Sci. 18, 179 to 190 (1987) equivalent to Chem. Abstracts 106 209425u.
Lang et al, Heteerocycl. Chem. 12(6), 1143 to 1153 (1975) equivalent to Chem. Abstracts 84 105503d.

*Primary Examiner*—John M. Ford
*Attorney, Agent, or Firm*—Herbert Dubno; Jonathan Myers

[57] ABSTRACT

The invention relates to novel tetrazine derivatives of the formula (I), wherein
X is fluorine, chlorine or bromine; and
Y is hydrogen or fluorine, as well as to a process for the preparation thereof.

Furthermore, the invention relates to compositions containing the above compounds as well as to a process for the preparation thereof. The compounds and compositions according to the invention have acaricidal; larvicidal an ovicidal effects.

8 Claims, No Drawings

ACARICAIDALLY ACTIVE TETRAZINE DERIVATIVES

SPECIFICATION

1. Field of the Invention

The invention relates to novel tetrazine derivatives and a process for their preparation. Furthermore, the invention relates to acaricidal compositions containing the novel compounds as well as to the preparation and use of these compositions. The compounds of the invention are effective against mites, their larvae and especially their eggs.

2. Background of the Invention

It is known that phytophagous mites are potentially the most important pests damaging the cultivated food-, industrial and ornamental plants as well as stored crops whereas ectoparasitic mites are severely dangerous from the viewpoint of public and veterinary hygiene. The loss caused by phytophagous mites has mounted quickly and the importance of protection to them has abruptly increased. This can essentially be attributed to two reasons:

1) The predators and parasites maintaining the mite populations below the threshold value of loss were thinned by the use of nonselective insecticides.

2) Due to the high number of generations and adaptability, a resistance of mites has developed within a relatively short period.

Typical representatives of harmful mite species in question are: spider mite (*Tetranychus urticae*), itch-mite (*Psoroptes cuniculi*), red spider mite (*Tetranychus cinnabarinus*) and other species hereinafter listed in detail.

Due to the increasing loss caused by mites, the development of highly effective, specific acaricides came into the limelight. For this purpose, a high number of tetrazine derivatives have been synthesized by various research groups (see the published European patent applications Nos 5912, 29657 and 248,466 as well as the Hungarian patent specification No. 184,684).

In the published European patent application No. 5912 several 3,6-bis(2-halophenyl)-1,2,4,5-tetrazines and 3,6-bis(2-halophenyl)-1,2-dihydro-1,2,4,5-tetrazines are disclosed, wherein the halogens, being the same or different for each compound, may be fluorine, chlorine or bromine. In the published European patent application No. 29657 a number of other 3,6-bis(2-halophenyl)-1,2,4,5-tetrazines and 3-(2,5-dichlorophenyl)-6-(2-chlorophenyl)- 1,2,4,5-tetrazine, too, are described. From these compounds 3,6-bis(2-chlorophenyl)-1,2,4,5-tetrazine described in the published European patent application No. 5912 became commercially available under the trade name Apollo® (clofentezine; Pesticide Manual 1987, page 188). Being inactive against adult individuals and nymphs as development stages of mites, clofenthesine is a selectively ovicidal compound. Among its advantageous properties, it is worth mentioning that it is selective (due to its novel mechanism of action), highly active, nontoxic to warm-blooded species, has a prolonged action and is essentially safe for useful living organism [Entomophaga 36, pages 55–67 (1991)].

However, despite many advantages of clofentezine, it is also known that it has a contact effect, is not absorbed through the leaf and consequently, it is ineffective against the unsprayed mite eggs being present e.g. on the abaxial surface of the leaf [Pestic. Sci. 18, pages 179–190 (1987)].

The complete coverage of the foliage is not assured practically in any case. Thus, compositions which can penetrate into the plant and be then translocated to the proper site, are only effective against pests living in a hidden manner of life or residing in a resting, immobile state at a safe site.

Based on the above knowledge, the aim of this invention is to develop an ovicidally active acaricide which, while possessing the favorable properties of clofentezine, exerts an additional excellent translaminar effect.

Thus, a high number of new tetrazine derivatives not described up to the present have been synthetized and the influence of modifications of the molecular structure on the translaminar acaricidal effect, especially the ovicidal effect was studied.

It has been found that 3,6-diphenyl-1,2,4,5-tetrazine derivatives of the formula (I),

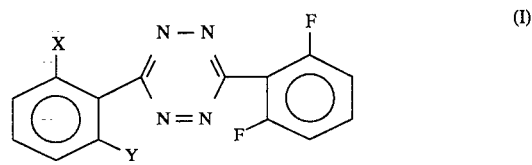

wherein

X means fluorine, chlorine or bromine; and

Y stands for fluorine or hydrogen, substituted by fluorine, chlorine or bromine in the ortho-position and containing fluorine or hydrogen in the ortho'-position of the 3-phenyl group as well as substituted by fluorine both in ortho- and ortho'-positions of the 6-phenyl group, possess an essentially new property, i.e. translaminar activity in addition to their stronger, inherent ovicidal effect. This bears a decisive importance for their practical utilization. Preferred representatives of the compounds of formula (I) are 3-(2-bromophenyl)-6-(2,6-difluorophenyl)-1,2,4,5-tetrazine, 3,6-bis(2,6-difluorophenyl)-1,2,4,5-tetrazine and 3-(2-chlorophenyl)-6-(2,6-difluorophenyl)-1,2,4,5-tetrazine as well as their tautomers.

In addition, the compounds of formula (I) according to the invention exert also a systemic effect namely, they act after being absorbed through the root and translocated into the sprout.

The advantages of the compound of the formula (I) of the present invention may be summarized as follows (but without any limitation thereto).

1) Their higher efficiency provides a lower specific dose and decreased load of the environment.

2) Due to their excellent translaminar activity, the mite eggs avoiding the spraying are also killed.

3) Due to their excellent transovarian effect, sterile eggs develop in the feeding females.

4) Their systemic action results in a significant broadening of the spectrum of effects and consequently of the scope of their employment.

5) Due to their longer duration of effect and transovarian activity, the times of optimum protection can be determined more easily from a technological point of view.

6) Due to their transovarian effect, they are useful for developing environment-sparing processes of plant protection (e.g. protection after harvesting).

The compounds of formula (I) or the compositions containing them, respectively give excellent results against *Tetranychus urticae, Tetranychus cinnabarinus, Tetranychus viennensis, Panonychus ulmi,* Bryobia and Schizotetranychus species belonging to the Tetranychus family; as well as against many species belonging to the Eriophydae and Tenuipalpidae families; furthermore, they can be employed with good results in all areas endangered by a loss caused by mites, e.g. in the protection of stores or in public and veterinary hygiene. In latter uses, the more important pests are exemplified by the Boophilus, Dermacentor, Ixodes, Rhipicephalus, Psoroptes and Sarcoptes species.

The compounds of formula (I) according to the invention can be transformed to compositions by using processes commonly known for plant-protective, pesticidal and veterinary hygienic formulations which can equally be applied onto plants, stored crops, soil and farm animals.

These compounds are soluble e.g. in water-immiscible solvents such as high-boiling hydrocarbons (e.g. xylene) as vehicles containing suitable emulsifying agents; thus, after being added to water, these compositions behave as self-emulsifying oils.

Alternatively, the substituted tetrazines may be mixed with a wetting agent and optionally with a solid carrier to obtain wettable powders that are soluble or dispersible in water or mixed with solid carriers, too, to prepare solid products.

An aqueous suspension concentrate may also be prepared by grinding the active ingredient together with water, wetting and suspending agent.

The surfactant may be ionic, anionic or cationic in its character.

Preferable surfactants are e.g. ethoxylated fatty alcohol sulfates, ligninsulfonates, alkylaryl sulfonates, salts of sulfonated naphthalene/formaldehyde condensates, salts of sulfonated phenol/formaldehyde condensates, sodium oleyl-N-methyltauride, dialkyl sulfosuccinates, alkylphenyl ethoxylates and fatty alkyl ethoxylates.

In addition to the substituted tetrazines, the compositions of the invention may contain also other active ingredients, e.g. insecticidal, acaricidal, ovicidal, bactericidal or fungicidal agents.

The compositions containing the active ingredients of formula (I) may be used at any site infested by mites or where the eggs or larvae of mites are present or expected to occur. The compositions according to the invention may be used e.g. on plants, animals or the soil.

Plants which can be treated with the compositions according to the invention are e.g.: sorts of cereals, plantation and ornamental plants such as cotton, tobacco, rice, fruit-trees and cereals, e.g. apple-tree, pear-tree, apricot-tree, peach-tree, citrus sorts, maize, barley or wheat, bean, sugar-beet, potato or carrot; or greenhouse plants and crops, e.g. pepper, tomato, cucumber, melon and strawberry.

For the various uses, the compositions containing the compounds of formula (I) may be employed in various amounts. Thus, 17 to 1120 g/hectare (g/ha) amounts of a composition may be applied onto the plant; or concentrations of 1 to 2000 ppm, preferably 100 to 1000 ppm, especially 35 to 280 g/ha of active agent may be used for killing the pests damaging the plants.

The novel compounds of formula (I) according to the invention can be prepared according to methods known in the art as described in detail in the published European patent application No. 5912.

Thus, the compounds of formula (I)

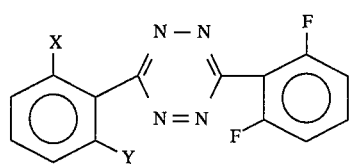

wherein

X means fluorine, chlorine or bromine; and

Y stands for fluorine or hydrogen, are prepared by a) reacting a substituted bis-azine of formula (II)

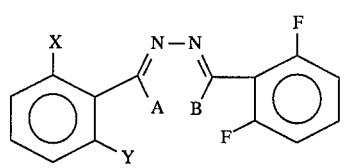

wherein X and Y are as defined above, and A as well as B stand for cleavable groups, with hydrazine of formula (III), $$H_2N-NH_2 \quad (III)$$

or the hydrate thereof, then oxidizing the obtained 3,6-disubstituted-1,2-dihydro-1,2,4,5-tetrazine of formula (IV),

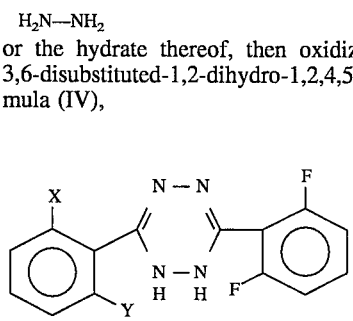

wherein X and Y are as defined above; or b) reacting an 1,3,4-thiadiazole derivative of formula (V),

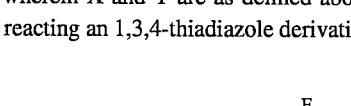

wherein X and Y are as defined above, with an alkyl sulfate of formula (VII)

$$R_2SO_4 \quad (VII)$$

wherein R represents a $C_{1-4}$ alkyl group, then transforming the obtained thiadiazolium salt of formula (VI),

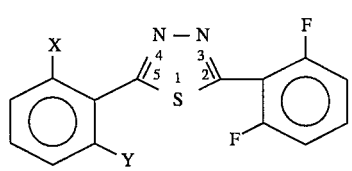

wherein X, Y and R are as defined above, with hydrazine of the formula (III) or the hydrate thereof, and subsequently oxidizing the resulting 3,6-disubstituted- 1,2-dihydro-1,2,4,5-tetrazine of formula (IV), wherein X and Y are as defined above; or c) oxidizing a 3,6-disubstituted-1,2-dihydro-1,2,4,5-tetrazine derivative of the formula (IV), wherein X and Y are as defined above.

The preparation of the starting compounds of formulae (II) and (V) from commercially available products is described in the published European patent application No. 5912.

The synthesis of the compounds of formula (I) as well as substances disclosed in the published European patent application No. 5912 used as reference substances is illustrated in detail in the following non-limiting examples.

Further examples show the preparation of compositions from compounds of the formula (I). The biological activity of compounds of formula (I) according to the invention is demonstrated in the Biological Examples.

The examples are only illustrative without any limitation thereto.

Chemical Examples

Example 1

3-(2-Bromophenyl)-6-(2,6-difluorophenyl)-1,2,4,5-tetrazine a.) N-(2-Bromobenzoyl)-N'-(2,6-difluorobenzoyl)hydrazine 0.94 g (1.05 equivalent) of 2,6-difluorobenzoyl chloride is added dropwise to a mixture containing 1.1 g of (2-bromobenzoyl)hydrazine, 3 ml of dimethylformamide and 0.5 ml of pyridine under cooling. The suspension obtained is stirred at room temperature for 30 minutes, then poured into water. The solid precipitate is separated by filtration and dried to give the desired product as white crystals in a yield of 1.35 g.

Analysis: calculated: C 47.35; H 2.55; N 7.89; Br 22.43; F 10.70%; found: C 47.38; H 2.41; N 7.88; Br 22.50; F 10.40%.

$^1$H-NMR (MeOD), ppm 7.07–7.12, 2H, t, 3- and 5-protons of Ar(2,6-F$_2$) 7.54, 1H, m, 4-protons of Ar(2,6-F$_2$) 7.68, 1H, dd, 3-proton of Ar(2-Br) 7.63, 1H, dd, 6-protons of Ar(2-Br) 7.39, 1H, dt, 4-protons of Ar(2-Br) 7.46, 1H, dt, 5-protons of Ar(2-Br)

$^{13}$C-NMR (MeOD), ppm Ar (2,6-F$_2$)—CO—NH 168.93 Ar (2-Br)—CONH 161.734

| Ar (2,6-F$_2$): | 1 | 114 | Ar (2-Br): | 1 | 137.55 |
|---|---|---|---|---|---|
| | 2, 6 | 162.54, 16.03 | | 2 | 120.07 |
| | 3, 5 | 112.81, 113.06 | | 3 | 134.40 |
| | 4 | 133.7 | | 4 | 128.86 |
| | | | | 5 | 130.50 |
| | | | | 6 | 132.85 | b.) N-[Chloro-(2-bromophenyl)methylene]-N'-[chloro-(2,6-difluorophenyl)methylene]hydrazine To a solution of 3.95 g of phosphorus pentachloride in 10 ml of carbon tetrachloride 1.35 g of product prepared in the preceeding step a.) are portionwise added over 5 minutes under boiling. After boiling the reaction mixture under reflux for 8 hours and evaporation of the excess of the solvent and phosphorous pentachloride, the residue is poured into 10% sodium hydroxide solution while cooling and then extracted with ethyl acetate. The organic phase is washed with water until neutral, dried over anhydrous magnesium sulfate and evaporated. The crude product is purified by column chromatography to give 0.96 g of desired product as snow-white crystals.

$^1$H-NMR (CDCl$_3$), ppm 7.00–7.06, 2H, t, 3- and 5-protons of Ar(2,6-F$_2$) 7.35–7.50, 4H, m, 4,5,6-protons of Ar(2-Br) and 4-protons of Ar(2,6-F$_2$) 7.61–7.72, 1H, dd, 3-proton of Ar(2-Br)

$^{13}$C-NMR (CDCl$_3$), ppm

Ar(2-Br)—C(=N—)—Cl  136.16
Ar(2,6-F$_2$)—C(=N—)—Cl  141.67

| Ar(2-Br): | 1 | 132.51 | Ar(2,6-F$_2$): | 1 | 113.61 |
|---|---|---|---|---|---|
| | 2 | 121.48 | | 2,6 | 158.85, 164.40 |
| | 3 | 132.61 | | 3,5 | 111.90, 112.14 |
| | 4 | 130.87 | | 4 | 132.61 |
| | 5 | 127.48 | | | |
| | 6 | 133.76 | | | | c.) 3-(2-Bromophenyl)-6-(2,6-difluorophenyl)-1,2-dihydro-1,2,4,5-tetrazine

To a solution containing 0.96 g of N-[chloro-(2-bromophenyl)methylene]-N'-[chloro-( 2,4-difluorophenyl)methylene]hydrazine [prepared in the preceeding step b.)] in 20 ml of tetrahydrofuran, 0.62 g of hydrazine hydrate is dropped at 40° C. temperature. The precipitate is filtered, washed with water and dried to obtain 0.62 g of desired product as yellow crystals.

d.) 3-(2-Bromophenyl)-6-(2,6-difluorophenyl)-1,2,4,5-tetrazine

A solution of 0.26 g of sodium nitrite in 1 ml of water is dropped to a solution containing 0.62 g of 3-(2-bromophenyl)-6-(2,6-difluorophenyl)-1,2-dihydro-1,2,4,5-tetrazine [prepared in the preceeding step c.)] in 2 ml of glacial acetic acid at room temperature under stirring. The progress of the reaction is followed by thin layer chromatography (TLC). The reddish-violet crystals are filtered, washed with water until neutral and dried to give 0.59 g of crystalline desired product, i.e. the title compound of Example 1. This crude product is recrystallized from a mixture of gasoline and acetone, m.p.: 168° C.

Analysis:

| | C | H | N |
|---|---|---|---|
| calculated: | 48.16 | 2.02 | 16.05 |
| found | 48.23 | 1.94 | 16.07 |

$^1$H-NMR (CDCl$_3$), ppm 7.16–7.26, 2H, t, 3- and -protons of Ar(2,6-F$_2$) 7.47–7.51, 1H, t, 4-proton of Ar(2-Br) 7.57–7.61, 1H, 5-proton of Ar(2-Br) 7.63, 1H, m, 4-protons of Ar(2,6-F$_2$) 7.83, 1H, d, 3-protons of Ar(2-Br) 8.05, 1H, d, 6-protons of Ar(2-Br)

$^{13}$C-NMR (CDCl$_3$), ppm

Ar(2-Br)—C(=N—)(N—)  160.65
Ar(2,6-F$_2$)—C(=N—)(N—)  165.85

| Ar(2-Br): | 1 | 132.95 | Ar(2,6-F): | 1 | ⁻114 |
|---|---|---|---|---|---|
| | 2 | 122.08 | | 2,6 | 159.45, |

| | 3 | 132.64 | 3, 5 | 162.00<br>112.02,<br>112.27 |
|---|---|---|---|---|
| | 4 | 132.14 | 4 | 133.68 |
| | 5 | 127.77 | | |
| | 6 | 132.16 | | |

Example 2

3,6-bis(2,6-Difluorophenyl)-1,2,4,5-tetrazine a.) N,N'-bis(2,6-Difluorobenzoyl)hydrazine 9.05 g of 2,6-difluorobenzoyl chloride and a solution of 2.17 g of sodium hydroxide in 7.5 ml of water are simultaneously dropped into a solution of 1.25 g of hydrazine hydrate in 25 ml of water under stirring and cooling by ice-water. After addition, the white suspension is stirred at room temperature for 2 hours. After filtration the solid product is washed with water and recrystallized from glacial acetic acid to yield 6.3 g of desired product as white crystals.
Analysis:

| | C | H | N | F |
|---|---|---|---|---|
| calculated: | 53.84 | 2.56 | 8.97 | 24.35 |
| found | 53.67 | 2.46 | 8.97 | 24.15 |

$^1$H-NMR (DMSO), ppm 7.24–7.67, 6H, m, Ar 11.00, 2H, s, NH $^{13}$C-NMR (DMSO), ppm

| CONH | 158.55 | |
|---|---|---|
| Ar (2,6-F$_2$) | 1 | 113.12 |
| | 2, 6 | 157.86, 159.80 |
| | 3, 5 | 112.01 |
| | 4 | 132.60 |

IR (KBr) $v_{OC=O}$=1640 cm$^{-1}$ MS M(+)=312 m/z.

b.) bis[Chloro-(2,6-difluorobenzylidene)]hydrazine

To a mixture containing 12.5 g of phosphorus pentachloride and 25 ml of carbon tetrachloride, 2 g of N,N'-bis(2,6-difluorobenzoyl)hydrazine [prepared in the preceeding step a.)] are portionwise added over 5 minutes while boiling under reflux. After boiling the reaction mixture under reflux for 8 hours carbon tetrachloride and phosphorus oxychloride are evaporated under reduced pressure. After adding ice-cold 10% sodium hydroxide solution, the residue is taken up in ethyl acetate, washed with water until neutral and evaporated. The crude product obtained is purified by column chromatography. By using a 10:1 mixture of gasoline and acetone as eluent, 0.9 g of desired product is obtained in the form of white crystals, m.p.: 142°–147° C.
Analysis:

| | C | H | N | Cl | F |
|---|---|---|---|---|---|
| calculated | 48.16 | 1.73 | 8.03 | 20.31 | 21.77 |
| found | 47.93 | 1.38 | 8.06 | 19.7 | 20.73 |

$^1$H-NMR (acetone-D6), ppm

| Ar (2,6-F$_2$) | 4 | 7.75 (m) |
|---|---|---|
| | 3, 5 | 7.29 (m) |

IR (KBr) $_{C=N}$=1630 cm$^{-1}$ MS M (+)=348 m/z $^{13}$C-NMR (acetone-D6), ppm Ar(2,6-F$_2$)—C(=N—)(Cl) 132.79

| Ar (2,6-F$_2$) | 1 | 113.29 |
|---|---|---|
| | 2, 6 | 158.79, 161.34 |
| | 3, 5 | 111.86, 112.08 |
| | 4 | 132.50 | c.) 3,6-bis(2,6-Fluorobenzoyl)-1,2-dihydro-1,2,4,5-tetrazine

To a solution of 0.9 g of bis[chloro-(2,6-difluorobenzylidene)]hydrazine [prepared in the preceeding step b.)] in 18 ml of tetrahydrofuran of 40° C. temperature, 0.59 ml of hydrazine hydrate is dropped during 1 minute. After filtering, the precipitate is washed with water and dried to give 0.5 g of desired product as yellow crystals.

d.) 3,6-bis(2,6-Difluorophenyl)-1,2,4,5-tetrazine

A solution of 0.12 g of sodium nitrite in 1 ml of water is added dropwise to the suspension of 0.4 g of 3,6-bis(2,6-difluorophenyl)-1,2-dihydro-1,2,4,5-tetrazine prepared in the preceeding step c.)] in 2.5 ml of glacial acetic acid at room temperature while stirring. The progress of the reaction is followed by thin layer chromatography. After filtration the carmine crystals are washed with water until neutral to give 0.34 g of desired product. This crude product is recrystallized from a mixture of gasoline and acetone to give 0.251 g of pure title product of Example 2, m.p.: 213.5° C.
Analysis:

| | C | N | H | F |
|---|---|---|---|---|
| calculated: | 54.91 | 18.30 | 1.97 | 24.82 |
| found | 55.09 | 18.34 | 1.82 | 25.00 |

$^1$H-NMR (CDCl$_3$), ppm 7.15–7.21, 4H, t, 3- and 5-protons of aromatic rings 7.58–7.65, 2H, m, 4-protons of aromatic rings $^{13}$C-NMR (CDCl$_3$), ppm Ar(2,6-F$_2$) C(=N—)(N—) 111.52

| Ar (2,6-F$_2$) | 3, 5 | 112.45 |
|---|---|---|
| | 2, 6 | 161.08 ($^1J_{CF}$ = 256.5 Hz) |
| | 4 | 133.72 |
| | 1 | 111.52 |

Example 3

3-(2-Chlorophenyl)-6-(2,6-difluorophenyl-1,2,4,5-tetrazine a.) N-(2-Chlorobenzoyl)-N'-(2,6-difluorobenzoyl)-hydrazine Step a.) of Example 1 is followed, except that 2 g of (2-chlorobenzoyl)hydrazine are used as starting substance instead of (2-bromobenzoyl)hydrazine to give 2.03 g of white, crystalline desired product.

Analysis:

|  | C | H | N | Cl | F |
|---|---|---|---|---|---|
| calculated | 54.12 | 2.92 | 9.02 | 11.41 | 12.23 |
| found | 53.85 | 2.86 | 9.05 | 11.05 | 11.63 |

$^1$H-NMR (DMSO), ppm 7.25–7.63, 7H, m, Ar 10.71, 1H, s, $^{Cl}$NH $^F$NH b.) Step b.) of Example 1 is followed, except that the product prepared in the preceding a.) is portionwise added to a solution of phosphorus pentachloride in carbon tetrachloride. After recrystallization the obtained product from a mixture of methanol and ethyl acetate, 1.26 g of white crystalline desired product are obtained, m.p.: 85°–92° C.

Analysis:

|  | C | H | N | Cl | F |
|---|---|---|---|---|---|
| calculated | 48.37 | 2.03 | 8.06 | 30.6 | 10.93 |
| found | 48.40 | 1.74 | 7.90 | 30.3 | 10.79 |

$^1$H-NMR (CDCl$_3$), ppm=6.99–7.67, 7H, m, Ar
$^{13}$C-NMR (CDC$_3$), ppm

| Ar(2-Cl) C(=N−)(−Cl) | 133.93 | Ar(2,6-F$_2$) C(=N−)(−Cl) | 140.55 |
|---|---|---|---|
| Ar (2-Cl): 1 | 131.68 | Ar (2,6-F$_2$): 1 | 113.47 |
| 2 | 132.71 | 2, 6 | 158.76, 161.3 |
| 3 | 131.68 | 3, 5 | 111.79, 112.0 |
| 4 | 130.79 | 4 | 132.53 |
| 5 | 130.49 |  |  |
| 6 | 126.80 |  |  |

IR (KBr) $v_{C=N}$=1627 cm−1 c.) Step c.) of Example 1 is followed. The crude product is oxidized without purification.

d.) The process described in Example 1 is followed. After recrystallization the pale violet product from ethyl acetate 0.7 g of pure title product of Example 3 is obtained, m.p.: 184.5° C.

Analysis:

|  | C | H | N | Cl | F |
|---|---|---|---|---|---|
| calculated | 55.19 | 2.32 | 18.39 | 11.64 | 12.47 |
| found | 55.05 | 2.19 | 18.28 | 10.94 | 12.22 |

$^1$H-NMR (CDCl$_3$), ppm 7.14–7.20, 2H, t, 3- and 5-protons of Ar(2,6-F$_2$) 7.51–7.66, 4H, m, 4,5,6-protons of Ar(2-Cl) and 4-protons of Ar(2,6-F$_2$) 8.0–8.11, 1H, dd, 3-proton of Ar(2-Cl)

$^{13}$C-NMR (CDCl$_3$), ppm

| Ar(2-Cl)—C(=N−)(−N−) |  | 160.87 |
|---|---|---|
| Ar(2,6—F$_2$)—C(=N−)(−N−) |  | 165.33 |
| Ar (2,6-F$_2$) | 1 | 111.58 |
|  | 2,6 | 159.71, 162.26 |
|  | 3,5 | 112.20, 112.45 |
|  | 4 | 133.50 |
| Ar (2-Cl) | 1 | 131.34 |
|  | 2 | 133.89 |
|  | 3 | 132.74 |
|  | 4 | 131.21 |
|  | 5 | 127.33 |
|  | 6 | 132.88 |

IR (KBr) $v_{C=N}$=1390 cm−1 (the N atoms are in aromatic heterocycle)

Reference Example 1

3,6-bis(2,6-Chlorophenyl)-1,2,4,5-tetrazine

Steps a.), b.), c.) and d.) of Example 2 are followed, except that 2-chlorobenzoyl chloride is used in step a.) instead of 2,6-difluorobenzoyl chloride.

Thus, 0.7 g of deep violet crystalline title compound is obtained, m.p.: 179°–182° C., which is identical in all respects with the target product of Example 14 of the published European patent application No. 5912.

Reference Example 2

3-(2-Chlorophenyl)-6-(2-bromophenyl)-1,2,4,5-tetrazine

Example 1 is followed by using in step a.) 2 g of 2-(chlorobenzoyl)hydrazine instead of 2-(bromobenzoyl)hydrazine and 2.7 g of 2-bromobenzoyl chloride instead of 2,6-difluorobenzoyl chloride. Thus, 0.6 g of reddish-violet crystalline title compound is obtained, m.p.: 168°–170° C., which is identical in all respects with the target product of Example 17 of the published European patent application No. 5912.

Analysis:

|  | C | H | N |
|---|---|---|---|
| calculated: | 48.37 | 2.32 | 16.12 |
| found | 47.40 | 2.18 | 15.40. |

$^1$H-NMR (CDCl$_3$), ppm 8.10–8.13, 1H, dd, 6-protons of Ar(2-Br) 8.06–8.08, 1H, dd, 6-protons of Ar(2-Cl) 7.83–7.85, 1H, dd, 3-protons of Ar(2-Br) 7.46–7.61, 1H, m, Ar(2-Cl)

Reference Example 3

3,6-bis(2-Chlorophenyl)-1,2-dihydro-1-methyl-1,2,4,5-tetrazine a.) N,N'-bis(2-Chlorobenzoyl)hydrazine Into a flask equipped with thermometer and bubbler, 0.7 g (0.014 mole) od hydrazine hydrate and 4 ml of water are weighed. In an other flask 1.2 g (0.03 mol) of sodium hydroxide are dissolved in 5 ml of water. The sodium hydroxide solution and 5 g (0.028 mol) of 2-chlorobenzoyl chloride are simultaneously added to the solution of hydrazine hydrate at such a rate that the temperature remains under 20° C. (cooling with water). A white precipitate appears. After stirring for additional 2 hours the white precipitate is filtered, washed with water and dried to give 5.04 g (57%) of desired product, m.p.: 218° C. after recrystallization from acetic acid.

b.) bis(alpha,2-Dichlorobenzylidene)hydrazine

To a boiling solution of 10.5 g (0.05 mol; 2.5 equivalents) of phosphorus pentachloride in 50 ml of carbon tetrachloride, 3.1 g (0.01 mol) of solid N,N'-bis(2-chlorobenzoyl)hydrazine are portionwise added. The boiling under reflux is continued until the starting substance is consumed according to thin layer chromatography (about 5 hours). For developing the TLC an 1:2 mixture of gasoline and acetone is used.

The product obtained is poured into the mixture of 50 g of ice and 50 ml of water, then stirred with 100 ml of methylene chloride. After separation the organic phase is washed with distilled water, dried and evaporated. The crude product obtained is recrystalliized from methanol to give 1.43 g (41%) of desired compound, m.p.: 102° C.

c.) 3,6-bis(2-Chlorophenyl)-1,2-dihydro-1-methyl-1,2,4,5-tetrazine

The suspension containing 3.74 g (0.026 mol) of methylhydrazine sulfate, 11.9 ml (0.086 mol) of triethylamine in 11.2 ml of abs. ethanol is boiled under reflux while portionwise adding 1.12 g (0.0032 mol) of bis(alpha,2-dichlorobenzylidene)hydrazine.

The reaction mixture is boiled under reflux for an additional 2 hours under stirring. After taking up the product in ethyl acetate, it is washed with water, dried and evaporated. A TLC analysis is carried out by using an 1:2 mixture of gasoline and acetone as developing system. The crude product weighing 0.90 g obtained is purified by column chromatography with a 3:1 mixture of gasoline and acetone as eluent. Thus, 0.48 g (48%) of desired compound is obtained, which is in complete agreement with the product described in Example 1 of the published European patent application No. 5912.

$^1$H-NMR (DMSO+$D_2O$), ppm 9.00, 1H, s, NH 7.37–7.58, 8H, m, Ar protons 2.68–2.71, 3H, s, Me Reference Example 4

3-(2-Chlorophenyl)-6-(2-bromophenyl)-1,2-dihydro-1-(or -2-)-methyl-1,2,4,5-tetrazine a.) N-(2-Chlorobenzoyl)-N'-(2-bromobenzoyl)hydrazine 2.7 g of o-bromobenzoyl chloride are added dropwise to a solution of 2 g of (2-chlorobenzoyl)hydrazine in 2 ml of dimethylformamide and 1 ml of pyridine under cooling. The suspension obtained is stirred at room temperature for an additional 30 minutes, then poured into water. The white crystalline precipitate is filtered and dried to 2.95 g of white crystalline desired compound.

b.) Step b.) of reference Example 3 is followed. After purifying the crude product by chromatography, 0.57 g of the title compound of Reference Example 4 is obtained which is in complete agreement with the compound described in Example 13 of the published European patent application No. 5912.

$^1$H-NMR (CDCl$_3$), ppm 7.26–7.65, 9H, m, aromatic protons and NH 3.00, 3H, s, Me Reference Example 5

3-(2-Chlorophenyl)-6-(2,6-dichlorophenyl)-1,2,4,5-tetrazine
N-(2-Chlorobenzoyl)-N'-(2,6-dichlorobenzoyl)tetrazine Example 1 is followed, by using in step a.) 1 g of (2-chlorobenzoyl)hydrazine instead of (2-bromobenzoyl)hydrazine and 1.47 g of 2,6-dichlorobenzoyl chloride instead of 2,6-difluorobenzoyl chloride to obtain 108 mg of pale violet crystals, m.p.: 88° C.

$^1$H-NMR 7.49–7.66, 6H, m, aromatic protons 8.11–8.14, 1H, d, aromatic protons

Analysis:

|  | C | H | N |
| --- | --- | --- | --- |
| calculated: | 49.8 | 2.09 | 16.6 |
| found | 49.58 | 1.88 | 16.54. |

Formulation Example 1

Wettable powders

Wettable powder compositions of 10, 20 or 50%, respectively are prepared from the active ingredients described in Examples 1, 2 or 3, respectively, by using 5% of wetting and dispersing agent as well as 85, 75 or 45%, respectively of kaolin as calculated for the weight of the composition.

Formulation Example 2

Suspension concentrates

Aqueous suspension concentrates are prepared, which contain 10, 20 or 50%, respectively, of active ingredient described in Example 1, 2 or 3, respectively, as well as 0.2 to 2% of xanthan gum, 5 to 10% of surface active agent and water as calculated for the weight of composition. Useful surface active substances may be ligninsulfonate, an ethoxylated fatty alcohol sulfate, alkylaryl sulfonate, a salt of sulfonated phenol-formaldehyde-condensate, an alkaline metal salt of ethoxylated citric acid, ethoxylated tartaric acid, ethoxylated citric/tartaric acid; triethylamine salt of citric/tartaric acid, sodium oleoyl-N-methyltauride, dialkyl sulfosuccinate, alkylphenyl ethoxylate or a fatty alcohol ethoxylate.

Formulation Example 3

Emulsifiable concentrates

Emulsifiable concentrates, which contain 5, 10 or 20%, respectively, by weight of the active ingredients described in Example 1, 2 or 3, respectively, and any of the surface active agents defined in Formulation Example 2 in an amount of 1 to 5% by weight calculated for the composition as well as mixtures of aliphatic or aromatic hydrocarbons as solvents in amounts supplementing the weight of composition up to 100%, are prepared.

Biological Example 1

Immersion ovicidal test on spider mite (*Tetranychus urticae*) by using active compounds Four adult female spider mites (*Tetranychus urticae* WHO sensitive strain) were placed on each leaf disk of 15 mm size cut out of young bean leaves. After an egg-laying lasting 24 hours at 26° to 28° C. the females were removed and the eggs laid on the disks were counted.

The treatments were carried out by immersing leaf disks into solutions containing appropriate concentrations of the active compounds (by using acetone as co-solvent in an amount of not higher than 5% in the test solution). The immersion lasted 5 seconds. After treatment, the disks were dried on dry filter paper, then maintained on wet filter paper at a temperature of 26° to 28° C. in a Petri dish until hatching out of the untreated control eggs and the ratio of hatching out was determined. Each experiment was carried out in four repetitions by using at least three parallels for each concentration. The effectivity values given for each concentration show the average of treatments performed at least on 250 mite eggs.

The corrected mortality was calculated according to Abbott by using the following formula:

Corrected mortality (%) =

$$\frac{\text{observed mortality minus control mortality (\%)}}{100 \text{ minus control mortality (\%)}}$$

The results expressed as percentages are shown in Table 1.

TABLE 1

| Concentration | Compounds tested according to No. of Example | | | | |
|---|---|---|---|---|---|
| | Ref. Ex. 4. | Ref. Ex. 3. | Ref. Ex. 2. | Ref. Ex. 1[a] | Example 3 |
| | Mortality % (Abbott)[b] | | | | |
| 0.06 | 0.5 | 3.6 | 1.0 | 1.8 | 19.0 |
| 0.12 | 1.5 | 5.0 | 15.9 | 20.6 | 60.0 |
| 0.25 | 5.0 | 7.1 | 41.7 | 59.2 | 94.3 |

[a]Clofenthesine was used as reference substance
[b]Related to the count of unhatched eggs Biological Example 2

Translaminar ovicidal test on spider mite (*Tetranychus urticae*) by using active compounds The right side of leaf of a bean plant (7 days old) was treated in such a way that the bean leaf was laid with its right side on the mouth of a glass cylindre of 20 ml volume containing 10 ml of test solution and exposed in an overturned position for 5 seconds. Then, the leaf was taken down from the glass cylindre and laid onto a wet, multilayer paper wadding in a Petri dish. The Petri dishes were kept at a temperature between 26° and 28° C. in a relative moisture content of 60 to 70% with a light/dark cycle of 16:8 ratio under a light intensity of 1600 lux. After 24 hours, disks of 15 mm in diameter were cut out of the treated surfaces, egg-laying was performed on the sides untreated, then the experiment was continued as described in Biological Example 1.

The results expressed as percentages are shown in Table 2.

TABLE 2

| Concentration (ppm) | Compounds tested according to No. of Example | | |
|---|---|---|---|
| | Ref. Ex. 1[a] | Ex. 2 | Ex. 3 |
| | Mortality % (Abbott)[b] | | |
| 400 | 18.9 | 100 | 100 |
| 200 | 18.3 | 100 | 100 |
| 100 | 11.4 | 100 | 100 |
| 50 | 7.7 | 100 | 95.8 |
| 20 | 4.7 | 84.8 | 91.8 |
| 10 | 0.0 | 71.3 | 66.7 |
| 5 | —[c] | 40.1 | 24.9 |

[a]Clofenthesine was used as reference substance

TABLE 2-continued

| Concentration (ppm) | Compounds tested according to No. of Example | | |
|---|---|---|---|
| | Ref. Ex. 1[a] | Ex. 2 | Ex. 3 |

[b]Related to the count of unhatched eggs
[c]Not tested

Biological Example 3

Transovarian test on spider mite (*Tetranychus urticae*) by using active compounds For adult female mites (*Tetranychus urticae*) for each dose were placed on a bean leaf disk treated as described in Biological Example 1 to feed the mites for 48 hours. Then, the mites were allowed to lay eggs on an untreated disk for 7 hours, the adults were removed and the eggs were counted. The disks were kept in a Petri dish on wet filter paper at a temperature between 26° and 28° C. until hatching out of the untreated control eggs and the ratio of hatching out was determined.

Each experiment was carried out in four repetitions with at least three parallels for each concentration. The effectivity values given for each concentration represent the average of treatments performed at least on 120 mite eggs.

The results expressed in percentage are shown in Table 3.

TABLE 3

| Concentration (ppm) | Compounds tested according to No. of Example | | |
|---|---|---|---|
| | Ref. Ex. 1[a] | Ex. 2 | Ex. 3 |
| | Mortality % (Abbott)[b] | | |
| 100 | 35.3 | 90.2 | 80.5 |
| 50 | 11.3 | 88.8 | 63.2 |
| 10 | 6.6 | 61.6 | 44.8 |

[a]Clofenthesine was used as reference substance
[b]Related to the count of unhatched eggs Biological Example 4

Ovicidal test on spider mite (*Tetranychus urticae*) by using compositions

The ovicidal effectivity of the 200 SC formulation prepared from the compound of Example 2 according to the Formulation Example 1 was tested as described in Biological Example 1. The results are shown in Table 4. The concentration relates to the active compound.

TABLE 4

| Concentration (ppm) | Apollo[R] 50 SC[a] | 200 SC |
|---|---|---|
| | Mortality % (Abbott)[b] | |
| 0.25 | 44.6 | 95.7 |
| 0.125 | 36.8 | 82.4 |
| 0.0625 | 18.5 | 62.1 |

[a]By using a reference composition containing clofenthesine
[b]Related to the count of unhatched eggs Biological Example 5

Translaminar ovicidal test on spider mite (*Tetranychus urticae*) by using compositions The translaminar effectivity of the 200 SC formulation prepared from the compound of Example 3 according to the formulation Example 2 was tested as described in the Biological Example 2. The results are shown in Table 5.

TABLE 5

| Concentration (ppm) | Apollo$^R$ 50 SC$^a$ | Sanmite$^R$ 15 EC$^b$ | 200 SC |
|---|---|---|---|
| | Mortality % (Abbott)$^b$ | | |
| 400 | 20 | 20 | 100 |
| 200 | 20 | 20 | 100 |
| 100 | 20 | 10 | 100 |
| 50 | 10 | 10 | 100 |
| 25 | 10 | 10 | 96.8 |
| 12.5 | 10 | 10 | 84.5 |
| 6.25 | 10 | 10 | 54.7 |

$^a$Reference composition containing clofenthesine
$^b$Reference composition containing pyridaben
$^c$Related to the count of unhatched eggs
pyridaben = 2-tert-butyl-5-(4)-terc-butyl-benzylthio)-4-chloro-pyridazin-3(2H)-one Biological Example 6

Ovicidal effectivity on the itch-mite (*Psoroptes cuniculi*)

From the scabs of ears of infected rabbits smaller pieces containing 50 to 100 itch-mite eggs were separated, immersed into the appropriate test solution and incubated at 34° C. for 48 hours. (At this time the ratio of hatching out of the untreated controls exceeded 90%.) Ethoxyethanol was used as co-solvent (in a concentration of not higher than 1% in the test solution).

After 48 hours the unhatched eggs were counted and the effectivity of treatments was expressed as percentage of the control. The effectivity of the active compound described in Example 3 and some anti-ectoparasitic compositions being important from the veterinary medicinal point of view expressed in percentages are shown in Table 6.

TABLE 6

| | | Concentration | |
|---|---|---|---|
| Active compound | Composition | 1000 ppm | 500 ppm |
| | | Mortality % | |
| Lindane | — | 25.6 | 9.5 |
| Amitraz | Mitac$^R$ | 18.7 | 0 |
| Phoxim | Sebacil$^R$ | 19.3 | 0 |
| Diazinon | Neocidol$^R$ | 15.4 | 2.4 |
| Target compound of Example 3 | — | 89.1 | 52.5 |

Chemical names:
Lindane: -1,2,3,4,5,6-hexachlorocyclohexane
Amitraz: N,N'-[(methylimino)-dimethylidene]-di(2,4-xylidine)
Phoxim: O,O-diethyl α-(cyanobenzylidene)amino(oxy-phosphorothioate)

TABLE 6-continued

| | | Concentration | |
|---|---|---|---|
| Active compound | Composition | 1000 ppm | 500 ppm |

Diazinon: O,O-diethyl-O-2-isopropyl-6-methylpyrimidin-4-yl phosphorothioate

What is claimed is:
1. A compound of formula (I),

$$\text{(I)}$$

wherein

X is fluorine, chlorine or bromine; and

Y is hydrogen or fluorine.

2. 3-(2-Bromophenyl)-6-(2,6-difluorophenyl)-1,2,4,5-tetrazine defined in claim 1.

3. 3,6-bis(2,6-Difluorophenyl)-1,2,4,5-tetrazine defined in claim 1.

4. 3-(2-Chlorophenyl)-6-(2,6-difluorophenyl)-1,2,4,5-tetrazine defined in claim 1.

5. Acaricidally, larvicidally and ovicidally active composition, which comprises 0.5 to 99% by weight of a compound of formula (I) as defined in claim 1, together with or more carrier(s), diluting, filling and/or surface active agent(s).

6. Method for diminishing the count of mites as well as larvae and eggs thereof, which comprises applying an acaricidally effective amount of a compound of formula (I), as defined in claim 1, to a locus infected by mites or larvae or eggs thereof or to a locus exposed to such infection.

7. An acaricidal composition with a translaminar or transovarian effect as defined in claim 5 wherein the compound of the Formula (I) is selected from the group consisting of:
3-(2-bromophenyl)-6-(2,6-difluorophenyl)-1,2,4,5-tetrazine;
3,6-bis(2,6-difluorophenyl)-1,2,4,5-tetrazine;
3-(2-chlorophenyl)-6-(2,6-difluorophenyl)-1,2,4,5-tetrazine; and mixtures thereof.

8. The method for diminishing the count of mites as well as larvae and eggs thereof defined in claim 6 wherein the compound of the Formula (I) is selected from the group consisting of:
3-(2-bromophenyl)-6-(2,6-difluorophenyl)-1,2,4,5-tetrazine;
3,6-bis(2,6-difluorophenyl)-1,2,4,5-tetrazine;
3-(2-chlorophenyl)-6-(2,6-difluorophenyl)-1,2,4,5-tetrazine; and mixtures thereof.

* * * * *

UNITED STATES PATENT AND TRADEMARK OFFICE
CERTIFICATE OF CORRECTION

PATENT NO: 5,455,237
DATED : 3 October 1995
INVENTORS: Janis HAJIMICHAEL et al It is certified that error appears in the above-identified patent and that said Letters Patent is hereby corrected as shown below:

column 1, line 54, for "clofenthesine" read -- clofentezine --;

column 5, lines 37 to 39 for

"Analysis Calculated: C 47.35; H 2.55; N 7.89; Br 22.43; F 10.70%; found: C 47.38; H 2.41; N 7.88; Br 22.50; F 10.40%" read -- Analysis:

|            | C     | H    | N    | Br    | F     |
|------------|-------|------|------|-------|-------|
| calculated | 47.35 | 2.55 | 7.89 | 22.43 | 10.70 |
| found      | 47.38 | 2.41 | 7.88 | 22.50 | 10.40 --| column 5, line 41, for "4-protons" read -- 4-proton --;

column 5, line 42, for "6-protons" read -- 6-proton --;

column 5, line 43, for "4-protons" read -- 4-proton --;

column 5, line 44, for "5-protons" read -- 5-proton --;

column 6, line 5, for "4-protons" read -- 4-proton --;

column 6, line 53, for "-protons" read -- 5-protons --;

column 6, line 55, for "4-protons" read -- 4-proton --;

column 6, line 56, for "3-protons" read -- 5-proton -- ;

column 6, line 57, for "6-protons" read -- 6-proton --;

column 6, line 65, for "Ar(2,6-F)" read -- Ar(2,6-$F_2$) --;

UNITED STATES PATENT AND TRADEMARK OFFICE
CERTIFICATE OF CORRECTION

PATENT NO: 5,455,237
DATED : 3 October 1995
INVENTORS: Janis HAJIMICHAEL et al

It is certified that error appears in the above-identified patent and that said Letters Patent is hereby corrected as shown below:

column 7, line 43, for " $\nu OC=O$ " read -- $\nu OC=O$ --;

column 8, line 1, for "(acetone-D6)" read -- (acetone-$D_6$)--;

column 8, line 7 for "C=N = 1630" read -- $\nu$ C=N = 1630 --;

column 8, line 8 for "(acetone-D6)" read -- (acetone-$D_6$)--;

column 8, line 21, for "3,6-bis(2,6-fluorobenzoyl)-1,2-dihydro-1,2,4,5-tetrazine" read -- 3,6-bis(2,6-difluorophenyl)-1,2-dihydro-1,2,4,5-tetrazine --;

column 9, line 31, for "ppm=6.99-7.67" read -- ppm 6.99-7.67 --;

column 9, line 47, for " $\nu$ C=N=" read -- $\nu$ C=N= --;

column 9, line 66, for "4-protons" read -- 4-proton --;

column 10, line 22, for " $\nu$ C=N=" read -- $\nu$ C=N= --;

column 10, line 27, for "3,6-bis(2,6-Chlorophenyl)-1,2,4,5-tetrazine" read -- 3,6-bis(2-Chlorophenyl)-1,2,4,5-tetrazine --;

column 10, line 40, for "2-(bromobenzoyl-)" read -- 2-(bromobenzoyl) --;

column 10, lines 54, for "6-protons" read -- 6-proton --;

column 10, lines 55, for "6-protons" read -- 6-proton --;

column 10, line 56, for "3-protons" read -- 3-proton --;

column 11, line 67, for "N-(2-Chlorobenzoyl)-N'-(2,6-dichlorobenzoyl)tetrazine" read -- N-(2-Chlorobenzoyl)-N'-(2,6-dichlorobenzoyl)hydrazine --;

column 12, line 7, for "protons" read -- proton --;

UNITED STATES PATENT AND TRADEMARK OFFICE
CERTIFICATE OF CORRECTION

PATENT NO: 5,455,237　　　　　　　　　　　　　　　Page 3 of 3
DATED　　: 3 October 1995
INVENTORS: Janis HAJIMICHAEL et al It is certified that error appears in the above-identified patent and that said Letters Patent is hereby corrected as shown below:

Column 13, line 29, for "Clofenthesine" read -- Clofentezine --;

Column 13, line 66, for "Clofenthesine" read -- Clofentezine --;

Column 14, line 38, for "Clofenthesine" read -- Clofentezine --;

Column 14, line 59, for "Clofenthesine" read -- Clofentezine --;

Column 15, line 19, for "5-(4)-terc-" read -- 5-(4-tert- --.

Signed and Sealed this

Tenth Day of March, 1998

*Attest:*

BRUCE LEHMAN

*Attesting Officer*　　　　*Commissioner of Patents and Trademarks*